United States Patent
Meehan et al.

(10) Patent No.: US 9,539,273 B2
(45) Date of Patent: *Jan. 10, 2017

(54) TARGETED DELIVERY OF ANTI-FUNGAL AGENTS

(71) Applicants: Thomas Meehan, El Dorado Hills, CA (US); Quyen Ong, Arcadia, CA (US)

(72) Inventors: Thomas Meehan, El Dorado Hills, CA (US); Quyen Ong, Arcadia, CA (US)

(73) Assignee: EDH Biotech Corp, El Dorado Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,371

(22) Filed: Jul. 7, 2015

(65) Prior Publication Data

US 2016/0058864 A1 Mar. 3, 2016

Related U.S. Application Data

(63) Continuation-in-part of application No. 13/958,547, filed on Aug. 3, 2013, now Pat. No. 9,089,134.

(51) Int. Cl.
  *A61K 47/24* (2006.01)
  *C07F 9/6521* (2006.01)
  *A61K 31/7048* (2006.01)
  *C07F 9/6558* (2006.01)
  *C07F 9/10* (2006.01)
  *A61K 47/48* (2006.01)

(52) U.S. Cl.
  CPC ..... *A61K 31/7048* (2013.01); *A61K 47/48061* (2013.01); *C07F 9/106* (2013.01); *C07F 9/65583* (2013.01)

(58) Field of Classification Search
  None
  See application file for complete search history.

*Primary Examiner* — Frederick Krass
*Assistant Examiner* — Celeste A Roney

(57) ABSTRACT

The present application discloses a targeting composition that actively targets chitin-like substances, such as those found in fungi, protists, arthropods, Alzheimer's plaques, etc. Methods are disclosed for preparation of chitin-targeted drug delivery vehicles composed of the targeting composition and one or more bioactive compounds.

12 Claims, No Drawings

TARGETED DELIVERY OF ANTI-FUNGAL AGENTS

CROSS-REFERENCE TO RELATED APPLICATIONS

This application claims the benefit of U.S. Provisional Patent Application Ser. No. 61/679,713, filed Aug. 4, 2012 and U.S. Non-Provisional application Ser. No. 13/958,547, filed Aug. 3, 2013, the disclosure of which is incorporated herein by reference in their entirety.

FIELD OF THE INVENTION

This application pertains to compositions for actively targeting bioactive agents to chitin or chitin-like materials, such as those in fungi, protists, and Alzheimer's plaques through use of stilbene-derived targeting groups.

SUMMARY OF THE INVENTION

The present application discloses stilbene-derived targeting agents that bind with high affinity to chitin and chitin-like substances and their use in preparing targeted nanoparticles encapsulating bioactive compounds.

BACKGROUND

Fungal blood stream infections are a serious problem with high morbidity and mortality. Blood stream infections from Candida albicans (among the most common), for example, often result from delayed or untreated local infections principally associated with the oral cavity, implants, surgical wounds, and the urinary tract. Fungal blood stream infections are dangerous and burdensome due to lengthened hospital stays, the need for expensive antifungal drugs, and high mortality rates (up to 40% for C. albicans). Furthermore, some of the most effective antifungal drugs exhibit serious side effects, including toxicity. Worldwide, fungal infections from pathogenic and opportunistic species are on the rise.

One of the most effective antifungal drugs, Amphotericin B (Am B), exhibits high toxicity, limiting its use and effectiveness. Efforts to reduce toxicity have included encapsulating Am B in nanoparticles, such as micelles, liposomes, and others. For example, U.S. Pat. No. 8,268,357, filed by Ryan and Oda, discloses particles for delivering drugs and other agents, the particles comprising a lipid binding polypeptide, a lipid bilayer and a non-polypeptide bioactive agent, and processes for making them.

US20110256213, filed by Onyuksel and Rubinstein, discloses a method of decreasing drug toxicity through use of sterically stabilized micelles or liposomes.

US20100210575, filed by Kwon and Vakil, discloses antifungal compositions comprising a derivatized Amphotericin B component such as Amphotericin B prepared with PEG-DSPE, where DSPE is distearoyl phosphatidylethanolamine, and methods of making and using them.

US20110256213, filed by Onyuksel and Rubinstein, discloses use of sterically stabilized micellar and liposomal compositions for the reduction or neutralization of endo-, exo- and other toxins associated with fungal and other agents, where the compositions can comprise water-insoluble antifungal agents.

US20100210575, filed by Kwon and Vakil, discloses inter alia PEG-distearoyl phosphatidylethanolamine (DSPE)/cholesterol micelle formulations to solubilize an antifungal agent, Amphotericin B, in combination with at least a second antifungal agent.

US20100062969, also filed by Onyuksel and Rubinstein, discloses a method of correcting oligopeptide misfolding through use of sterically stabilized micelles comprising a hydrophilic polymer-conjugated lipid or sterically stabilized mixed micelles (SSMM) of a hydrophilic polymer-conjugated lipid and a water-insoluble lipid, an example of the former is distearoylphosphatidylethanolamine-polyethylene glycol 2000 (DSPE-PEG$_{2000}$).

Each of the following cited patents, U.S. Pat No. 8,268,357, US20110256213, US20100210575, US20100062969, are hereby incorporated by reference in their entirety.

Passive delivery of Amphotericin B has been accomplished by solubilization of the drug in deoxycholate (Fungizone). This is also the most toxic form of the drug. More recent passive delivery formulations include lipid complexes from Sigma-Tau (Abelcet), colloidal dispersions from Three Rivers Pharmaceuticals (Amphotec), and liposomes from Gilead (AmBisome) and Lifecare Innovations (Fungisome). Some of these formulations reduce toxicity, but do not eliminate it. Other passive delivery formulations under development include micelles, block co-polymer micelles, nano-spheres, and others. In passive delivery, the serum concentration of drug (and drug carrier) must be high enough to permit diffusion of sufficient drug to the site of infection deep inside tissues to eliminate the infection.

A superior approach is the use of targeted delivery. In this strategy, the toxic drug is encapsulated in a vehicle whose surface is modified with an agent that has high affinity for the site of the disease, such as a fungal infection.

Targeted delivery results in the drug (and carrier) accumulating at the site of infection, driven by interaction between the targeting agent and its target site in the fungal organism. With our invention, high affinity binding of the targeting agent to chitin fungal components thermodynamically drives accumulation of the drug at the site of infection, against a concentration gradient (low serum concentration and high infection site concentration). This substantially reduces the amount of antifungal drug in the blood stream compared to that necessary in passive delivery, thereby permitting therapeutic, and even prophylactic, use of highly effective, but otherwise toxic, antifungal drugs

SUMMARY OF THE INVENTION

Current technology focuses on antigen-antibody reagents for targeted drug delivery. Drawbacks to this approach include lability of reagents and size limitations in navigating the vasculature network. The applicants have found that the binding of certain stilbene-derived small organic derivatives to chitosan, a model for chitin in fungal cells, yields a surprisingly strong interaction, so strong that it is comparable with antigen-antibody interactions. This feature of the stilbene-derived derivatives is, therefore, useful for targeting purposes, in particular, for targeting drug encapsulated particles to fungi. The advantages of the stilbene-derived targeting agents include high target affinity, stability, non-toxicity, and small molecular size.

DETAILED DESCRIPTION OF THE INVENTION

Unless otherwise specified, technical terms take the meanings specified in the McGraw-Hill Dictionary of Scientific and Technical Terms, 6th edition.

As used here,

"alkyl" either alone or in a phrase such as "alkylamino" refers to a saturated hydrocarbon group having one to 12 carbon atoms;

"alicyclic" refers to a saturated cyclic hydrocarbon having three to 12 ring carbon atoms;

"alkoxy" refers to a saturated hydrocarbon group having one to 12 carbon atoms attached singly to oxygen;

"heterocyclic" refers to three- to seven-membered rings in which at least one carbon atom is replaced by an atom selected from the group consisting of N, O, and S;

"aryl" refers to an aromatic hydrocarbon having six to 12 ring carbon atoms;

"heteroaryl" refers to aromatic groups having five to 12 ring atoms, at least one of which is selected from the group consisting of N, O, and S;

"fatty acid" refers to saturated or unsaturated carboxylic acids having six or more carbon atoms, with "fatty acid acyl group" referring to the acyl group derived from such fatty acid;

"phospholipid" refers to a compound containing a glycerol backbone esterified with two fatty acids and a phosphate, and the latter can be further substituted by simple organics, including ethanolamine, serine, inositol, inositol phosphate, glycerol, glycerol phosphate or choline.

Fungi express chitin in their cell walls, a component unique to pathogenic and other fungi and, thus, not generally found in mammals (although chitin-like material has been found in Alzheimer's plaques and suspected in cancer cells; see for example 1-4). Chitin is an oligomer of glucose in which the 2-hydroxyl group of glucose is replaced with an acetylated amino group (NH-Ac) and the monomers are linked together linearly or branched in a (1→4)-β-D-configuration. Chitin newly synthesized in a fungal cell wall is thought to have relatively high solubility in water, unlike aged chitin, and in this and other respects more closely resembles chitosan, which is a 70-80% deacetylated version of chitin. Chitin-like materials also include cellulose, another closely related biopolymer made up of glucose units with (1→4)-β-D-linkages. By analogy to chitin, binding to cellulose was measured employing a soluble form of the biopolymer, methyl 2-hydroxyethyl cellulose (MHEC). The stilbene optical brighteners exhibit a similar high affinity for soluble cellulose, MHEC, as they do for chitosan. Stilbene optical brighteners bind to mixed biopolymers of any structure that contain elements of chitin or cellulose oligomers of sufficient length. The term "chitin-like materials" as used here refers collectively to chitin, chitosan, cellulose, or mixed biopolymers with elements of chitin, chitosan or cellulose, or any chitin-like materials (for example, Alzheimer's plaques or certain synthetic polyols) exhibiting high affinity for stilbene optical brighteners.

Chitin and cellulose were long ago observed qualitatively to bind certain optical brighteners, compounds used in laundry detergents and other applications to increase the apparent brightness of cloth, paper, and other objects. Chitin occurs widely in fungi and other organisms, including insects, shellfish, and eukaryotic microorganisms, including algae and protists (but, generally, not mammals). In addition to plants, cellulose occurs in some microorganisms, including bacteria. Many of the most commonly used optical brighteners, such as calcofluor white, are derived from stilbene. The binding of these optical brighteners to chitin, chitosan, and cellulose has long been considered a laboratory curiosity, but the applicants in quantifying this effect have found a surprisingly strong interaction ($K_d' \, 10^{-9}$ to $10^{-8}$ M), one comparable to the binding between many antigens and antibodies (5-7).

Here we describe additional approaches for synthesizing and assembling stilbene-derived, targeted nanoparticles that encapsulate antifungal drugs, such as Amphotericin B, for targeted drug delivery to organisms containing chitin-like substances.

The optical brightener structures associated with high affinity for chitin-like molecules (chitin and chitosan and cellulose) feature stilbene cores, in particular 4,4'-diaminostilbene-2,2'-disulfonic acid, although neither the core structure itself nor its bis(dichlorotriazine) derivative ($R^{4a}$=$R^{6a}$=$R^{4b}$=$R^{6b}$=Cl) binds to chitosan (see Table 1).

Structure of the Targeting Agent

Accordingly, this application discloses a targeting agent (TA) for targeting chitin-like materials, including, chitin, chitosan, and cellulose, the agent having the structure

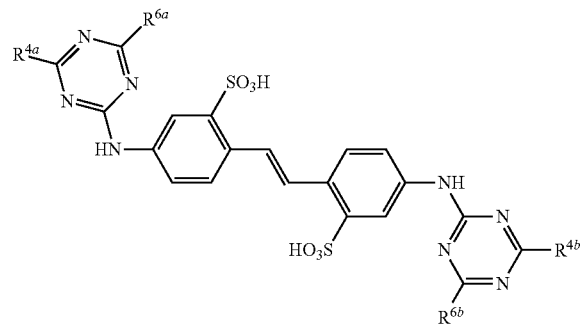

wherein $R^{4a}$, $R^{4b}$, and $R^{6a}$ are independently selected from Cl, amino, or hydroxy, the last two of which are optionally substituted by alkyl, alkylamino, alkylhydroxy, alicyclic, heterocyclic, aryl, and alkyl- or arylsulfonic acid, where each of the optional substituents may further be optionally substituted by one or more groups selected from the group consisting of hydroxy and amino, wherein $R^{6b}$ is linked to (i) phospholipid-PEG$_n$, where the number of PEG units, n, is about 10-250, (ii) phospholipid, or (iii) dendrimer (G$_3$-G$_{10}$), wherein the linker is composed of PEG, alkyl, heteroalkyl, heterocyclic, or aryl, and pharmaceutically acceptable salts thereof.

Targeting Agent Modification of Passive Drug Delivery Vehicles

The antifungal drug is encapsulated in a passive drug delivery nanoparticle (NP), such as a micelle, liposome, nanodisc, or dendrimer. The surface groups of passive delivery vehicles are functionalized with amino or carboxyl groups, or any other reactive group. The passive delivery vehicle is transformed into an actively targeted drug delivery agent by surface modification with functionalized targeting agent. To accomplish this, the targeting agent is asymmetrically synthesized. Three of the four positions located at $R^{4a}$, $R^{6a}$, $R^{4b}$, or $R^{6b}$ in the targeting agent are modified with any of the following groups Cl, amino, or hydroxy, the last two of which are optionally substituted by alkyl, alkylamino, alkylhydroxy, alicyclic, heterocyclic, aryl, and alkyl- or arylsulfonic acid, where each of the optional substituents may further be optionally substituted by one or more groups selected from the group consisting of hydroxy and amino; the fourth position is occupied by a chloro group. The chloro group undergoes nucleophilic substitution with a bifunctional linker (for example, diaminopropane) that, in turn, is covalently attached to a drug carrying nanoparticle. The order of assembly between targeting group, linker, and passive delivery vehicle is unimportant.

The linker-modified optical brightener-propylamine (OBPA) targeting agent has a single amino-functionalized position that is then coupled to a passive drug delivery NP. An OB-targeted dendrimer is made by reacting the OBPA with amino or carboxyl surface-modified dendrimers, followed by Am B encapsulation with the targeting agent modified dendrimer. An actively targeted block copolymer micelle, such as phospholipid-polyethylene glycol (PEG) is self-assembled following reaction of OBPA with, for example, distearoylphosphatidylethanolamine-polyethylene glycol amine (DSPE-PEG-$NH_2$). Reaction of OBPA directly with DSPE results in OBPA-modified DSPE that self assembles into liposomes bearing encapsulated Am B. This same intermediate, OBPA-DSPE, will self-assemble into nanodiscs (NDs) in the presence of phospholipids and Apolipoprotein A1 (ApoA1). The targeted NDs also encapsulate Am B and other antifungal drugs. We have synthesized numerous OB derivatives employing other linkers, such as polyethylene glycols, linear alkyl chains, alkylaromatics, or heterocycles. Each of these derivatives exhibits high affinity for chitin-like materials and are suitable as targeting agents.

Binding of Targeting Agent

Binding studies of stilbene derivatives to chitosan or MHEC

TABLE 1

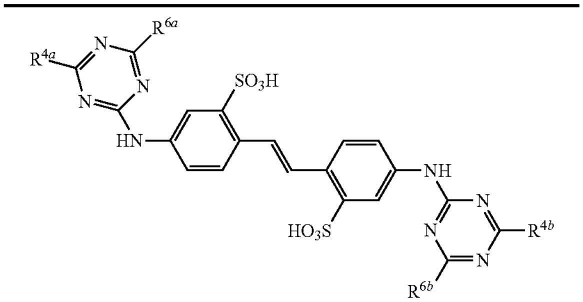

| Stilbene Derivative | $R^{6a}/R^{6b}$ | $R^{4a}/R^{4b}$ | $K_d'$ |
|---|---|---|---|
| bis(4,6-dichlorotriazine) | Cl | Cl | Nil |
| bis(6-chloro-4-anilinotriazine) | Cl | NHPh | $4.70 \times 10^{-9}$ |
| bis(6-aminoalkyl-4-anilinotriazine) | aminoalkyl | NHPh | $2.53 \times 10^{-8}$ |
| (6-PE-6-aminoalkyl)bis(4-anilinotriazine) | PE + aminoalkyl | NHPh | $2.43 \times 10^{-8}$ |
| (6-$PEG_{2000}$PE-6-aminoalkyl) bis(4-anilinotriazine) | $PEG_{2000}$PE; aminoalkyl | NHPh | $7.01 \times 10^{-8}$ |

PE = phosphatidylethanolamine; $PEG_{2000}$ = polyethylene glycol with an average MW = 2000 revealed that substituent size and composition at positions $R^{4a}$, $R^{4b}$, $R^{6a}$, and $R^{6b}$ had little effect on binding affinity (Table 1). Even a single, very large, bulky substituent located at either $R^{4a}$, $R^{4b}$, $R^{6a}$, or $R^{6b}$ was tolerated. Replacing the 4,4'-chloro groups in the bis(dichlorotriazine) with 2 eq of aniline to gave ($R^{4a}$=$R^{4b}$=NHPh; $R^{6a}$=$R^{6b}$=Cl), a stilbene derivative that resulted in high affinity binding to chitosan. Further substitution of the remaining 2 chloro groups with an alkyl amine gave the common OB calcofluor white (CFW) ($R^{4a}$=$R^{4b}$=NHPh; $R^{6a}$=$R^{6b}$=N$(CH_2CH_2OH)_2$, OB85 ($R^{4a}$=$R^{4b}$=NHPh; $R^{6a}$=$R^{6b}$=$NHCH_2CH_2OH$), or the asymmetric optical brightener propylamine (OBPA) ($R^{4a}$=$R^{4b}$=NHPh; $R^{6a}$=N$(CH_2CH_2OH)_2$; $R^{6b}$=$NHCH_2CH_2CH_2NH_2$) that affords no significant improvement in binding.

Replacement of only one of the chloro groups of the bis(chloroanilinotriazine) ($R^{4a}$=$R^{4b}$=NHPh, $R^{6a}$=$R^{6b}$=Cl) with distearoyl phosphatidylethanolamine (DSPE) or DSPE-PEG2000, while the other chloro position exhibits alkylamine, resulted in only small changes to the apparent dissociation constants ($K_d'$) of these derivatives. This finding showed that a single asymmetric bulky modification of the triazine in optical brighteners, which are used to synthesize targeted nanoparticles of the invention, exert little or no adverse effect on targeting affinity.

The binding of stilbene-derived groups of the invention to chitin-like materials, including chitin and cellulose, resulted in a large absorbance red-shift (~30-35 nm), permitting use of an indirect difference spectroscopy method (8, 9) for measurement of dissociation constants. Saturation analysis by a filtration assay validated the accuracy of the difference spectroscopy method for determining binding constants in the calcofluor white-chitosan system ($K_d'$=1.62-3.74×$10^{-8}$ M by saturation analysis, 2.02-5.45×$10^{-8}$ M by difference spectroscopy, both at the 95% confidence interval).

Saturation analysis of maximum binding suggested the number of saccharide residues per binding site is 8, in reasonable agreement with the 9-12 residues from the difference spectroscopy method.

TA-100

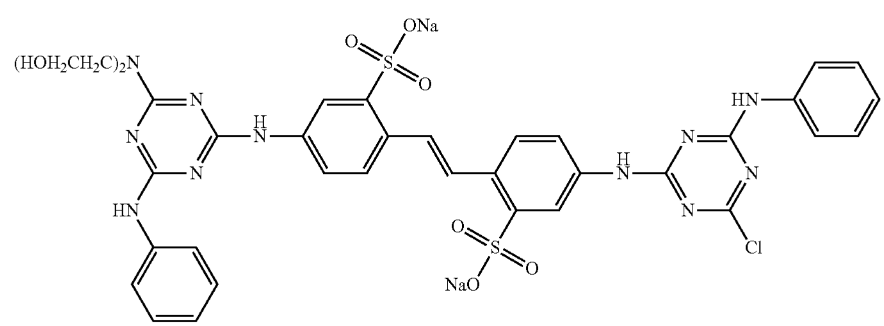

Efficient targeting assembly requires that a synthetic scheme is employed for making a stilbene intermediate with only a single functionalized chloro position, for example, targeting agent TA-100:

Drug Delivery Vehicles

One embodiment of the present invention employs targeting agent-modified block copolymer micelles comprised of targeting agent-PEG-phospholipid for targeted delivery of antifungal drugs. Other multi-block copolymers could readily serve to form targeted micelles.

In another embodiment, targeting agent-phospholipid was combined with lipoprotein A to form chitin-targeted nanodiscs.

In another embodiment, targeting agent-phospholipid was sonicated to form chitin-targeted liposomes.

In another embodiment, targeting agent was employed to modify the functionalized surface of dendrimers to form chitin-targeted dendrimers.

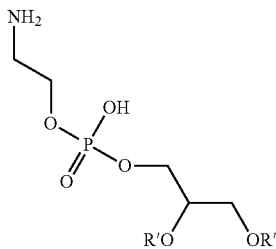

Some of the targeted drug delivery vehicles of the present invention, such as micelles, liposomes, or nanodiscs, include phospholipids bearing one or more targeting agents, as defined above, and that comprise one or more phospholipids such as the well-known phosphatidylethanolamine (often abbreviated "PE"), have the general structure where the R' groups are independently selected from fatty acid acyl groups. Other phospholipids can substitute, as the choice of phospholipid is not critical. As will be appreciated by those skilled in the art, phospholipids of the generic structure F—R—OP(O)(OH)OCH$_2$CH(OR')CH$_2$ (OR'), where F comprises a functional group, such as primary or secondary amine, carboxyl, OH, or phosphate groups, and R a connecting group, and R' a fatty acid, and optionally including one or more sites of unsaturation, are generally suitable for use in the present invention.

Pathogenic Fungi

The targeting agents and drug delivery vehicles of the present invention are useful in connection with administering bioactive compounds to any pathogenic or opportunistic fungi, including those from the genera *Candida, Aspergillus, Cryptococcus, Histoplasma, Pneumocystis, Coccidioides Mycetoma, Paracoccidioides*, and *Stachybotrys*, each of which is among prominent fungal pathogens. Species such as *C. albicans, Aspergillus fumigatus, Aspergillus clavatus, Cryptococcus neoformans, Cryptococcus laurentii, Cryptococcus albidus, Cryptococcus gattii, Histoplasma capsulatum, Pneumocystis carinii, Stachybotrys chartarum* warrant specific mention in this connection.

Anti-Fungal Drugs

Anti-fungal drugs that may be used according to the present invention include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Polygodial, Tolnaftate, Undecylenic acid, although other drugs may also be used.

Other Applications

This invention is useful for the targeted delivery of drugs or other agents to kill or otherwise influence any organism that contains chitin-like material, including chitin or cellulose. Some of these applications include agricultural or veterinary uses, in particular for controlling the spread of fungal infections. Healthy plants are treated externally with targeted drug carriers encapsulating food-grade antifungals to eliminate or prevent the spread of surface infection by pathogenic fungi. The invention is also useful against certain protozoan parasites (for example, Giardia that spread disease by shedding chitin containing cysts through feces and Trichomonas vaginalis, a widespread venereal disease, where the organism does not form cysts but does contain chitin on the surface of the free living form), and chitin containing algae (the delivery of anti-algal drugs for containing red tide or other algal blooms). Chitin-like material has been reported in human Alzheimer's plaques (1-4) and these sites could be targeted with stilbene-modified NPs capable of crossing the blood-brain-barrier and encapsulating bioactive compounds.

Pharmaceutically Acceptable Salts

Many of the compounds here are disclosed as acids, bases, or salts, but those skilled in medicinal chemistry will appreciate that the choice of salt is not critical, and other pharmaceutically-acceptable salts can be prepared by well-known methods. Handbook of Pharmaceutical Salts: Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499 discuss such salts in detail.

More generally, those skilled in the art will appreciate that a variety of prodrugs, salts, hydrates, solvates, and polymorphs can be produced from the compounds disclosed here, and that various isotopically-substituted variants (through, e.g., substitution of deuterium for hydrogen, $^{13}$C for carbon, $^{15}$N for nitrogen) can also be readily produced. All such derivatives are contemplated within the scope of this disclosure.

EXAMPLES

Targeting Enhancement

In principle, those skilled in the art will realize that targeting agents of the present invention are readily incorporated into several related types of particles, such as micelles, nanodiscs, liposomes, and dendrimers resulting in conversion of passive delivery vehicles into actively targeted delivery vehicles. Phospholipids or the surface positions of dendrimers in the inventive drug delivery vehicles can carry one or more targeting agents, such as those related to 100, with additional targeting agents covalently attached in a linear array to each other through short linkers. Use of such multiple pendent targeting groups typically enhances binding affinity by several orders of magnitude through the chelate effect, just as it does in antigen-antibody binding (6, 10). Those skilled in the art will realize that single or multiple pendency is contemplated within the scope of this disclosure.

Asymmetric Synthesis of Targeting Agent (TA)

The synthesis of TA-100 serves as a general example for asymmetric synthesis of a targeting agent intermediate and is summarized as follows:

1) 1 eq cyanuric acid (CyA) (5-10° C., 2-3 h, pH 4.5)

2) 1 eq aniline (6-68° C., 1.5 h, pH 7)

3) 15 eq DEOA (70-75° C., 1.5-2 h, pH 8)
4) 12 eq Fe-0.3 M AA (30-40 min, 90-95° C.)
5) 1 eq CyA (5-10° C., 2-3 h, pH 4.5)
6) 1 eq aniline (65-68° C., 1.5 h, pH 7)

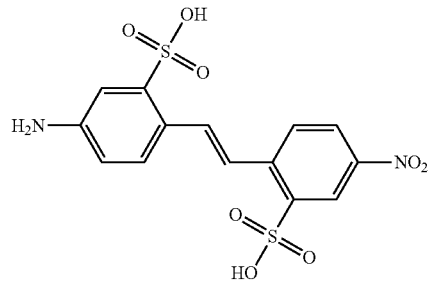

4-nitro-4'-amino-Stilbene-Disulfonic
Acid (starting material)

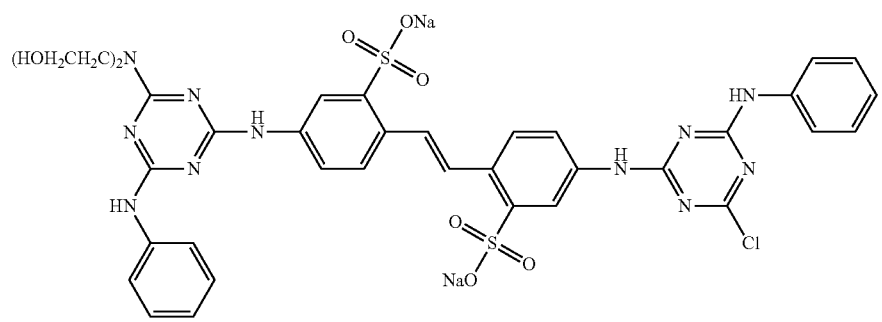

TA-100

Progress in each step of the synthetic sequence was followed by TLC.

Step 1: The synthetic sequence was initiated with the commercially available 4-nitro-4'-amino-stilbene-2,2'-disulfonic acid. Ten grams of the starting material was treated with 1 eq of cyanuric acid. The cyanuric acid was dissolved in 34 mL methyl ethyl ketone and added to 15 mL water in a 250 mL Erlenmeyer, with vigorous stirring on an ice bath, over a 5 min period. The stilbene derivative was dissolved in 100 mL water containing 2 eq $Na_2CO_3$ and added to the cyanuric acid at 0° C. over 1 h, while the pH was maintained at 5-5.5 with 4 N NaOH. After the addition, the reaction was stirred an additional hour at 0° C. and, finally, after removing the reaction flask from the ice bath, for 1 more hour while the mixture slowly warmed to room temperature.

The reaction flask was stored overnight at 4° C. The product formed a heavy red-brown precipitate that was filtered (Whatman #50) and the precipitated cake transferred to a 250 mL Erlenmeyer and re-suspended in 150 mL water.

Step 2: The pH of re-suspended product of step 1 was adjusted to 7.0 with 4 N NaOH and 1 eq of aniline added with stirring over 5 min. The sample was then heated in an oil bath to 65-68° C. and stirred for 2 h, while maintaining the pH between 7-7.5 with NaOH. After cooling to room temperature, 10% solid NaCl was added to precipitate the product. The precipitate was collected on Whatman #50 filter paper and the precipitate re-suspended in 200 mL water in a 500 mL flask.

Step 3: The pH of the product of step 2 was adjusted to 8 with 4 N NaOH and 15 eq of diethanolamine (DEOA) added drop wise over 5 min at room temperature. The flask was heated in an oil bath to 70-75° C. for 2 h with stirring. The product was precipitated by the addition of 10% solid NaCl. The collected precipitate was washed with a 5% NaCl, then water, and re-suspended in 200 mL water.

Step 4: The nitro group was reduced to the corresponding amine by treatment with iron filings (about 6 eq or 12 g) in 40 mL water containing 3.4 mL glacial acetic acid (final concentration of acetic acid about 0.3 M). The filings were heated to 80° C. for 15 min in a 1 L flask and stirred. The temperature of the flask was raised to 100° C. and the product of step 3 (after adjusting the pH to 5) was added to the heated flask. The liquid suspension was maintained at 90-95° C. for 30-40 min. The flask was removed from the heat and cooled to 60° C. The pH of the sample was adjusted to 7.5 and filtered through Whatman #50 paper (using a preheated filtration funnel) to remove insolubles, mainly iron filings. The product was salt precipitated and the sample stored at 4° C. overnight.

Step 5: The single amine group remaining in the product of step 4 was modified with cyanuric acid as described in step 1.

Step 6: One of the chloro groups in the product of step 5 was replaced with an aniline group as described in step 2. After the product was salt precipitated, the wet cake was transferred to a tared round bottom flask, and dried at 70° C. on a rotary evaporator. Compound TA-100 weighed 1.5 g for an overall yield of 15%, based on the amount of starting material, for the six steps in the synthesis. The structure of TA-100 was established by ESI-MS and NMR.

Other Examples

By simple replacement of nucleophiles in either steps 2, 3, and/or 6, numerous other targeting agents were made. Substitutions made at step 2, in general, require pH 7-7.5 and temperatures of 65-68° C. A 1:1 ratio is employed between the stilbene derivative and nucleophile in step 2, because exceeding 1:1 results in significant reaction at site 6a. Substitutions made at step 3 or 6, in general, require pH 8-8.5 and tempertures of 70-75° C. Stoichiometry at step 6 is also limited to 1:1, however, excess nucleophile is employed at step 3 because there is only one reactive site at this stage.

Replacement of DEOA in step 3 with 25% aqueous ammonia during the synthesis of TA-100 produced TA-101. The reaction mixture in step 3 was heated near 75° C. for 2-2.5 h. The remainder of the synthesis and workup was as described for TA-100.

TA-101

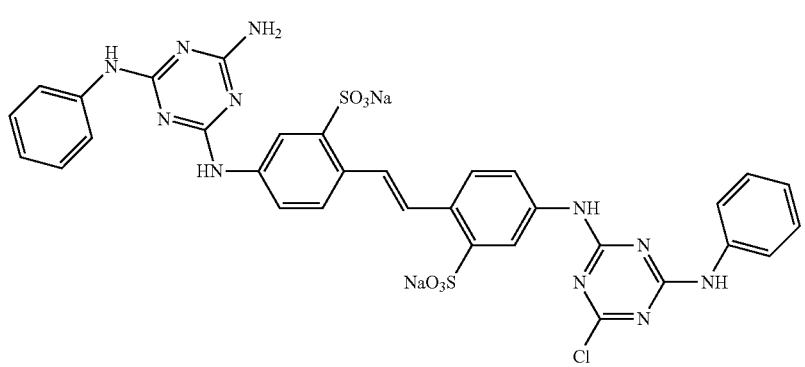

Replacement of DEOA in step 3 with 5 mM NaOH during the synthesis of TA-100 produced TA-102. The reaction mixture was heated near 75° C. for 2-2.5 h in step 2. The remainder of the synthesis and workup was as described for TA-100.

Replacement of aniline (step 6) in the synthesis of TA-100 with 1 equivalent of cyclohexylamine generated TA-104. The reaction mixture in step 6 was heated to 65-68° C. for 1.5-2 h and the pH maintained between 7-7.5. The remainder of the synthesis and workup was as described for

TA-102

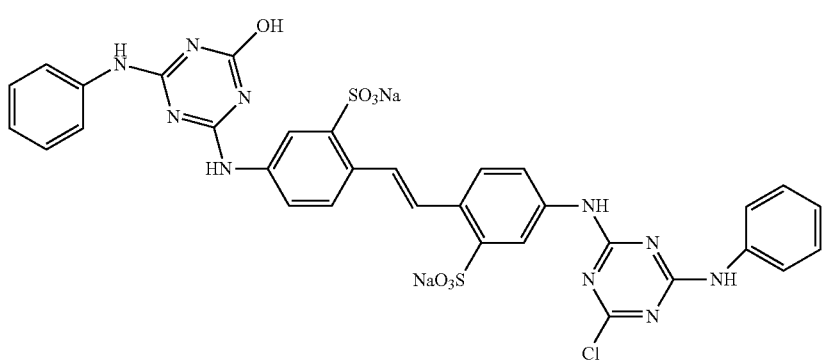

Replacement of DEOA (step 3) with 10 equivalents of ethylamine during the synthesis of TA-100 formed TA-103. The reaction mixture in step 3 was heated to 75° C. for 1.5-2 h and the pH maintained between 8-8.5. The remainder of the synthesis and workup was as described for

TA-103

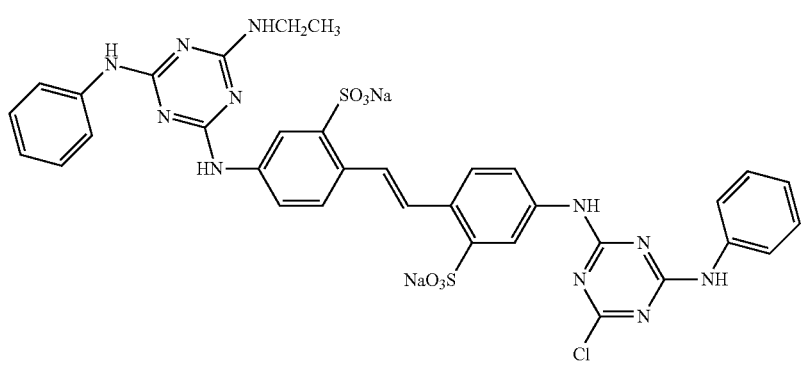

TA-100.

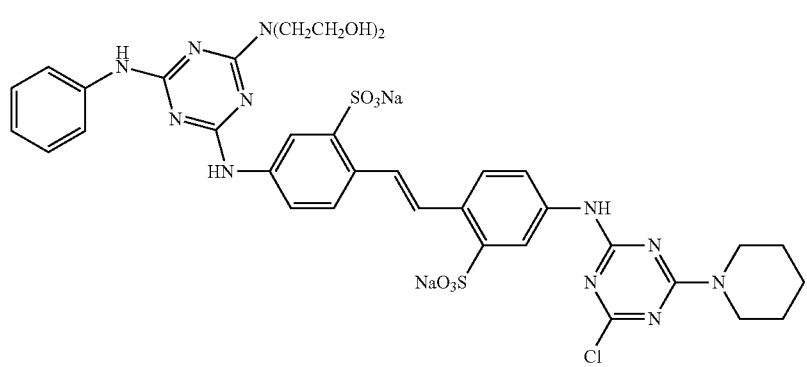

TA-104

TA-100.
Replacement of aniline (step 2) with 1 equivalent of piperazine and DEOA for aniline (step 6) in the synthesis of TA-100 generated TA-105. The reaction mixture in step 2 was heated to 65-68° C. for 1.5-2 h and the

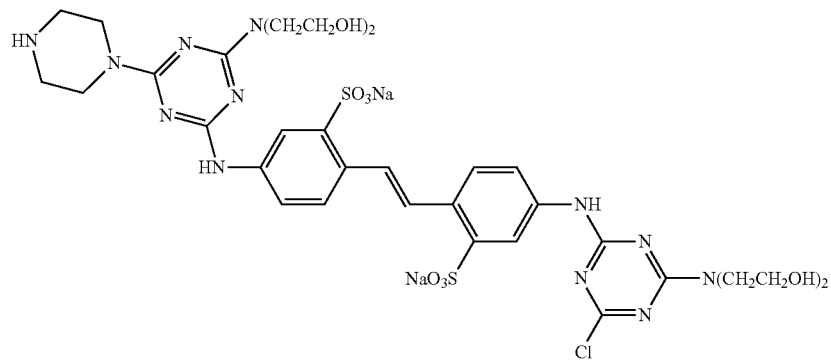

TA-105 pH maintained between 7-7.5. The remainder of the synthesis and workup was as described for TA-100.

Replacement of aniline (step 2) with 1 equivalent of sulfanilic acid and DEOA for aniline (step 6) in the synthesis of TA-100 formed TA-106. In step 2, the reaction mixture was heated to 65-68° C. for 1.5-2 h and the pH maintained between 7-7.5. The remainder of the synthesis and

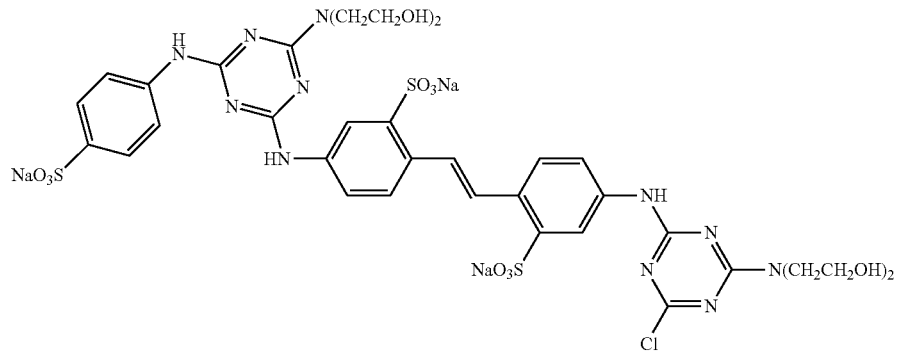

TA-106 workup was as described for TA-100. Additional sulfonic acid groups in TAs increase water solubility, but with 4 or more, a decrease in binding affinity to the ~$10^{-7}$ M range was observed that, however, is still sufficient for targeting purposes.

Replacement of DEOA (step 3) with 12 equivalents of β-alanine and DEOA for aniline (step 6) in the synthesis of TA-100 generated TA-107. The reaction mixture in step 3 was heated to 75° C. for 2-2.5 h and the pH

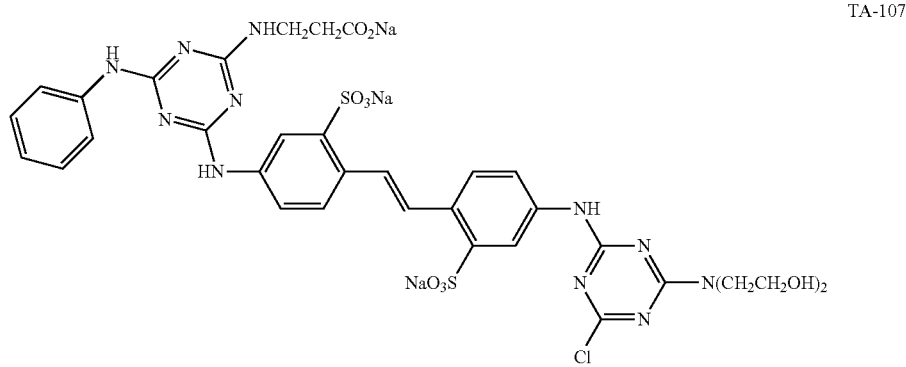

TA-107 maintained between 8-8.5. The remainder of the synthesis and workup was as described for TA-100.

Replacement of aniline (step 2) with 1 equivalent of p-anisidine and DEOA for aniline (step 6) in the synthesis of TA-100 formed TA-108. In

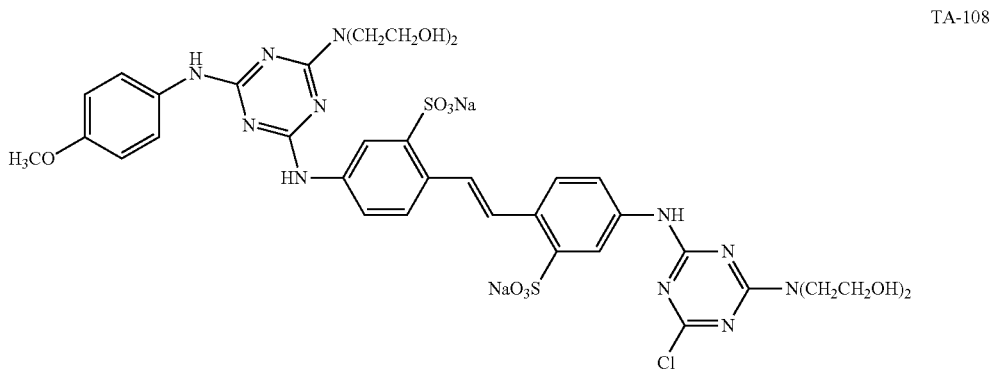

TA-108 step 2, the reaction mixture was heated to 65-68° C. for 1.5-2 h and the pH maintained between 7-7.5. The remainder of the synthesis and workup was as described for TA-100.

Replacement of aniline (step 2) with 1 equivalent of 1-amino-2-methoxyethane and DEOA for aniline (step 6) in the synthesis of TA-100

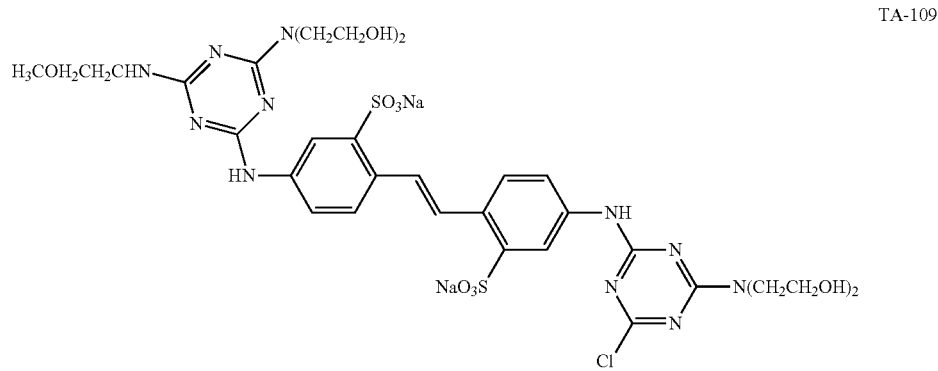

TA-109 produced TA-109. The reaction mixture in step 2 was heated to 65-68° C. for 1.5-2 h and the pH maintained between 7-7.5. The remainder of the synthesis and workup was as described for TA-100.

Replacement of DEOA (step 3) with 10 equivalents of

TA-110

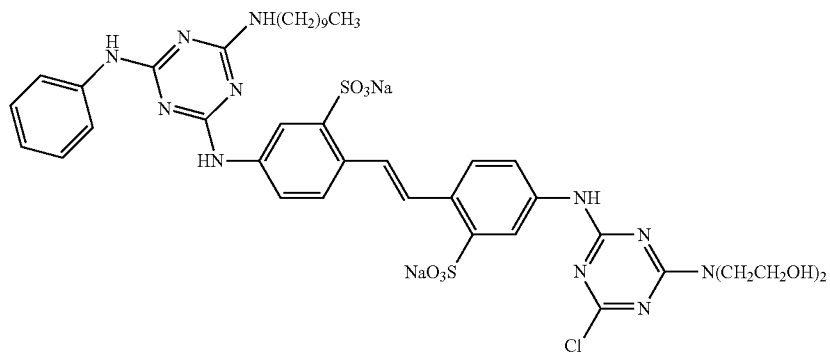

1-aminodecane and DEOA for aniline (step 6) in the synthesis of TA-100 yielded TA-110. In step 3, the reaction mixture was heated to 75° C. for 2-2.5 h and the pH maintained at 8-8.5. The remainder of the synthesis and workup was as described for TA-100.

We have employed many other substitutions at $R^{4a}$, $R^{4b}$, and $R^{6a}$ with additional nucleophiles (see claim 1 for examples) and, in all cases, high affinity target binding was maintained (binding constants in the range of $10^{-7}$ to $10^{-9}$ M). These substitutions had little influence with regard to chitin targeting. More generally, those skilled in the art will appreciate that a variety of other compounds can also be readily produced by reacting other nucleophiles at the $R^{4a}$, $R^{4b}$, and $R^{6a}$ positions. All such derivatives are contemplated within the scope of this disclosure. Some of these derivatives do, however, provide flexibility in adjusting the water solubility of the targeting agent, an important consideration for self-assembly of nanoparticles, such as micelles liposomes, and nanodiscs, but less so for pre-formed nanoparticles, for example dendrimers.

Adding Linkers to the TAs

Linkers were added to the TAs by nucleophilic substitution of the final chloro group located at $R^{6b}$ (see structure TA-100). In these instances, the reaction conditions were those outlined in step 3 for the synthesis of TA-100. Higher pH (8-8.5) and elevated temperature (>70° C.) was required to effectively substitute the final chloro groupon a triazine moiety (11).

Examples of TA Linkers

Linkers must be bifunctional to effect their purpose of joining the TA and a passive delivery vehicle. In the first example, 30 equivalents of diaminopropane (DAP) was added to TA-100 in water at a pH of 8-8.5. The reaction was initiated by the adding the diamine drop wise at room temperature. The temperature was raised to 70-75° C. and the reaction stirred for at least 1.5 h (some linkers require longer reaction times). After cooling to room temperature, 10% NaCl was added and the mixture stored at 4° C. overnight. The precipitate formed was collected on Whatman #50 filter paper and washed with 10% salt, water, and a small amount of acetone. The sample was resuspended in water pH 7 and the precipitation carried a second time. The second precipitate was dried and weighed. Conversion of TA-100 to TA-111 was nearly quantitative.

TA-111

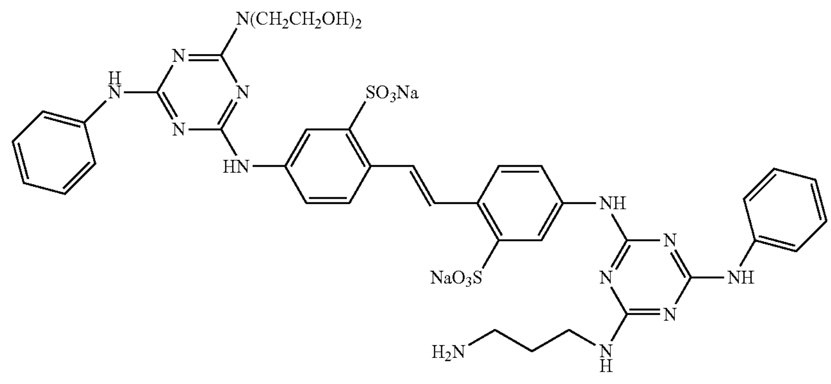

A significant reduction in $R_f$ of TA-111 compared to TA-100 on TLC and a modest ninhydrin reaction supported the introduction of the propylamine group into the product. The structure of TA-111 was verified by ESI-MS ($MH^+$ expected 898.30, obtained 898.31, $MNa^+$ expected 920.30, obtained 920.29). The $H^1$ NMR spectrum of TA-111 was consistent with the proposed structure.

Other Diamino Linkers

When DAP was replaced in the synthesis of TA-111 with 15 equivalents of 1,8-diaminooctane, TA-112 was formed, a $C_8$ diaminoalkyl linker.

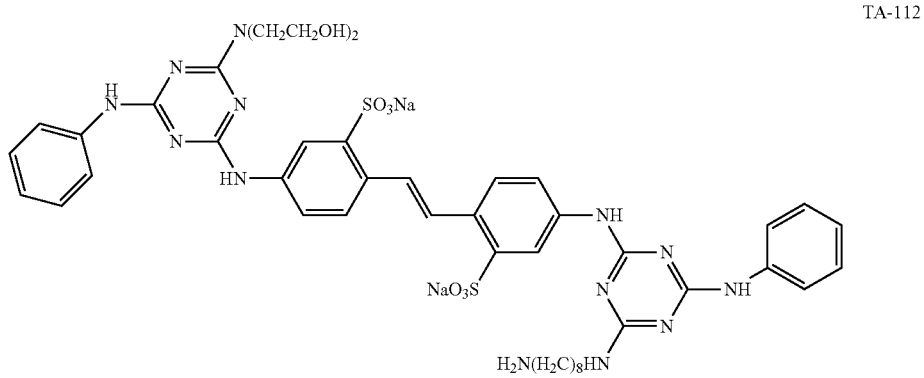

TA-112

When DAP was replaced in the synthesis of TA-111 with 15 equivalents of 1,12-diaminododecane, TA-113 was generated, a $C_{12}$ diaminoalkyl linker.

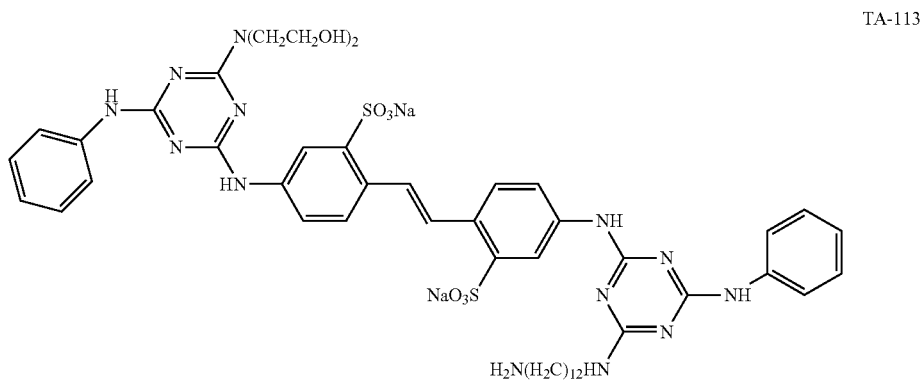

TA-113

When DAP was replaced in the synthesis of TA-111 with 15 equivalents of diethylenetriamine, TA-114 was generated, a tribasic linker.

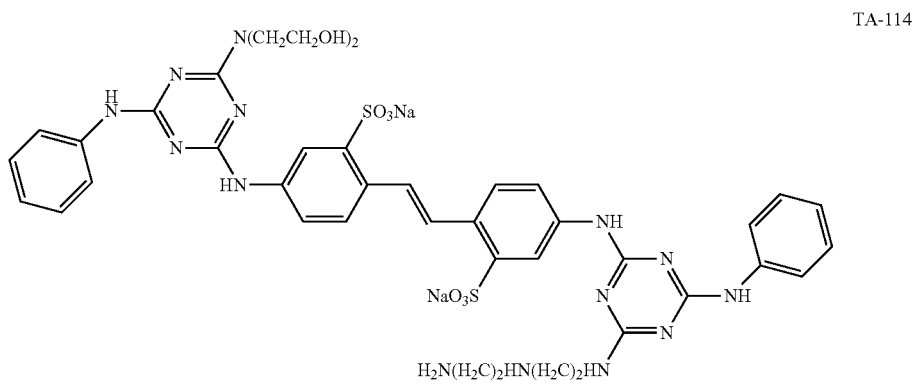

TA-114

When DAP was replaced in the synthesis of TA-111 with 15 equivalents of 4,4'-diaminodiphenylmethane, TA-115 was generated, a diaminoarylalkyl linker.

TA-115
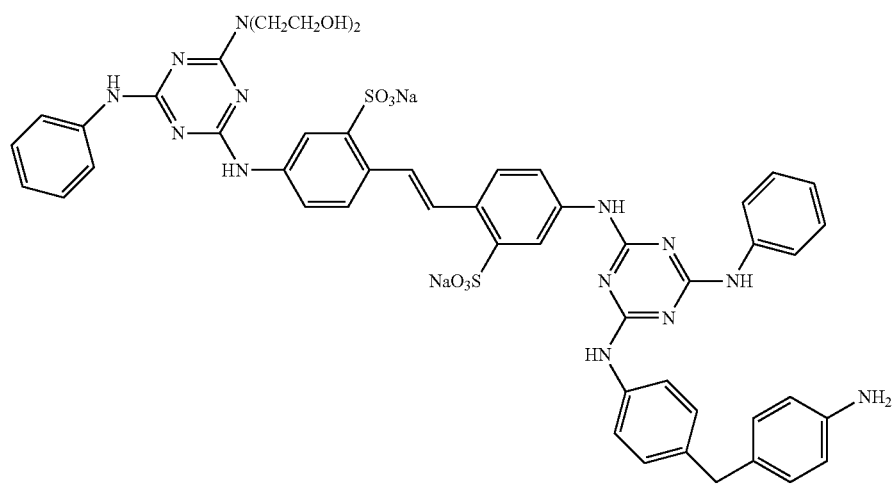
Amino Acid Linkers
When DAP was replaced in the synthesis of TA-111 with 15 equivalents of β-alanine, TA-116 was generated. In the case of amino
TA-116
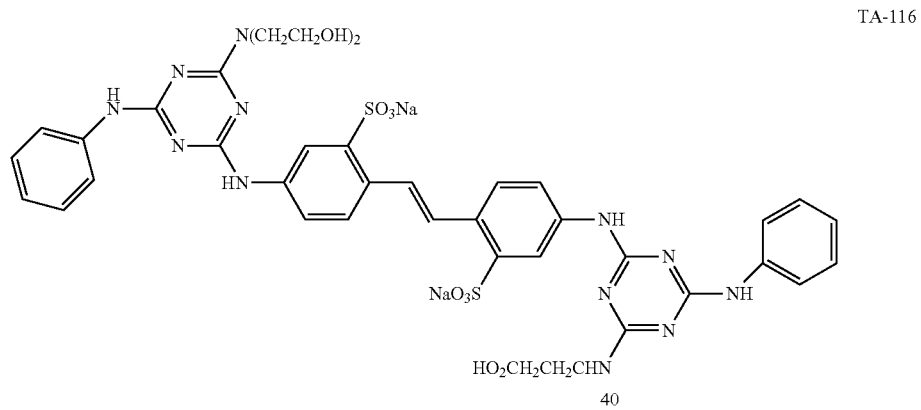
acids, a carboxyl group was employed in the final linking step to passive delivery vehicles.
When DAP was replaced in the synthesis of TA-111 with 15 equivalents of 4-aminobenzoic acid, TA-117 was generated.
TA-117
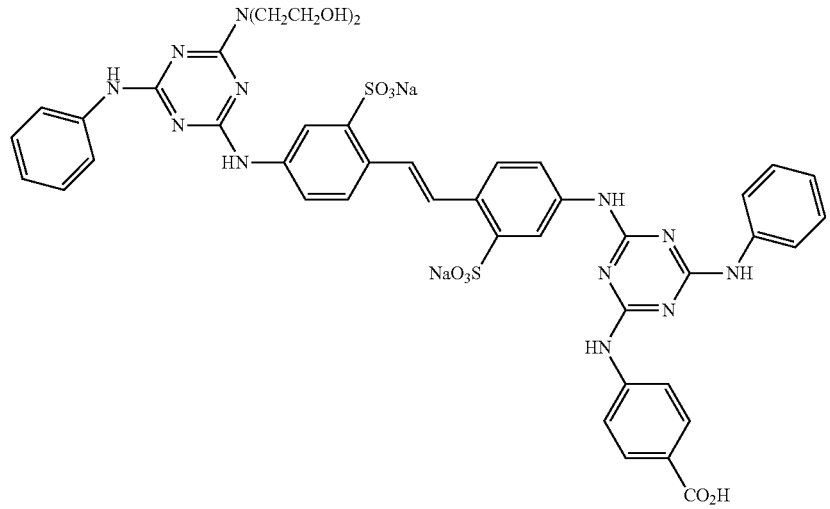

Polyethylene Glycol (PEG) Linkers

When DAP was replaced in the synthesis of TA-111 with 10 equivalents of $NH_2$-$PEG_{2000}$-$NH_2$, TA-118 was generated. The temperature of the PEG-linker reactions was maintained near 65° C. and reaction time extended to 2.5-3 h. TA-118 was isolated by the same approach used for TA-100.

By analogous procedures, $NH_2$-$PEG_{3500}$-$NH_2$, $NH_2$-$PEG_{5000}$-$NH_2$, and $NH_2$-$PEG_{7500}$-$NH_2$ were substituted at the single chloro position in TA-111, formimg TA-119, TA-120, and TA-121, respectively.

Targeting Agent-Modified Phospholipids

DSPE-PEG2000-$NH_2$ (100 mg) was dissolved in 3 mL MeOH along with 6 eq TEA and 1.2 eq of DSC. The reaction was stirred for 2 h at room temperature. The activated phospholipid was then added to 3 mL DMF containing 20 eq TA-111 and 3 eq TEA. The reaction was stirred at 35° C. for 48-72 h. Reaction progress was monitored by TLC. When no further change was observed the sample was stored at −20° C. The product, DSPE-$PEG_{2000}$-TA-111 (TA-122), separated out from the MeOH/DMF (1:1 at −20° C.) to form a dense gel-like material that settled to the bottom of the tube over 24-48 h. The upper solvent layer was drawn off and the process repeated 1 or 2 times more, until the solvent was nearly colorless. After a final purification by preparative TLC (silica gel, C/M/3% $NH_4OH$, 75/20/2 v/v/v X 2 developments) the sample was concentrated, dried, and weighed. The PEG-lipid was joined to the stilbene derivative via a urea (or carbamide) linkage. Overall yield was 24% (based on DSPE-$PEG_{2000}$-$NH_2$). The structure of TA-122 was established by MALDI-TOF MS and NMR.

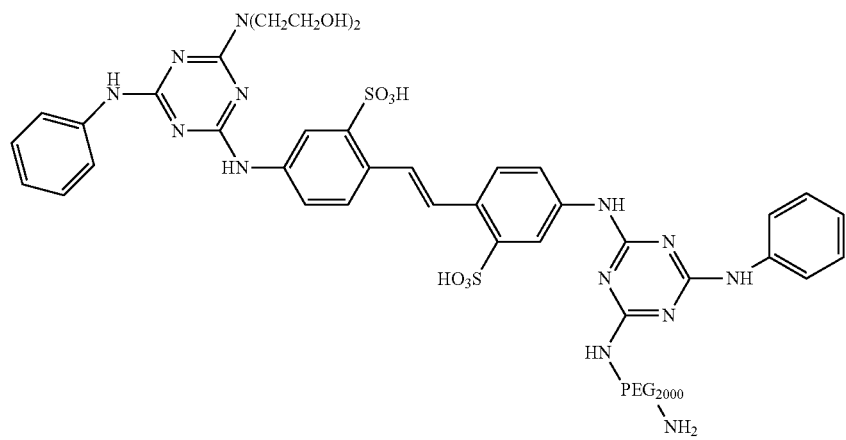

TA-118

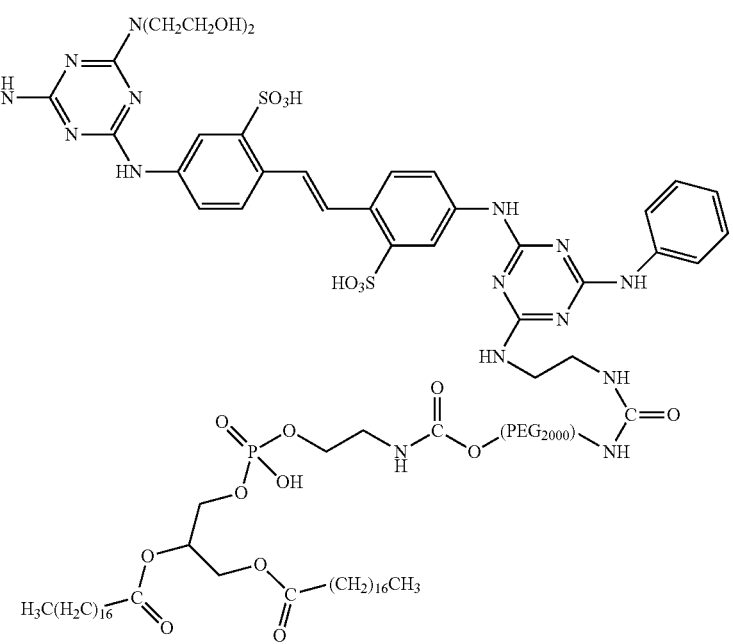

TA-122

By substitution of DSPE-PEG$_{2000}$-NH$_2$ with DSPE-PEG$_{2000}$CO$_2$H, TA-123 was synthesized where the linkage between the PEG and stilbene derivative was an amide, as opposed to carbamide in TA-122. DSPE-PEG$_{2000}$-CO$_2$H was activated as its NHS ester employing DSC but, in this case, the solvent was THF and the base was N-methylmorpholine (NMM). The coupling temperature and time was about the same as in the synthesis of TA-122.

activated under conditions similar to those employed for DSPE-PEG$_n$-NH$_2$, however, CHCl$_3$ was the solvent and TEA was the base. TA-118, -119, -120, or -121 were dissolved in MeOH and added individually to activated DOPE. The reaction was stirred at 35° C. for 48-72 h, resulting in the formation of TA-124-TA-127. The TA-modified PEG-phospholipids were isolated by procedures outlined for TA-122. The structure of TA-124 serves as an

TA-123

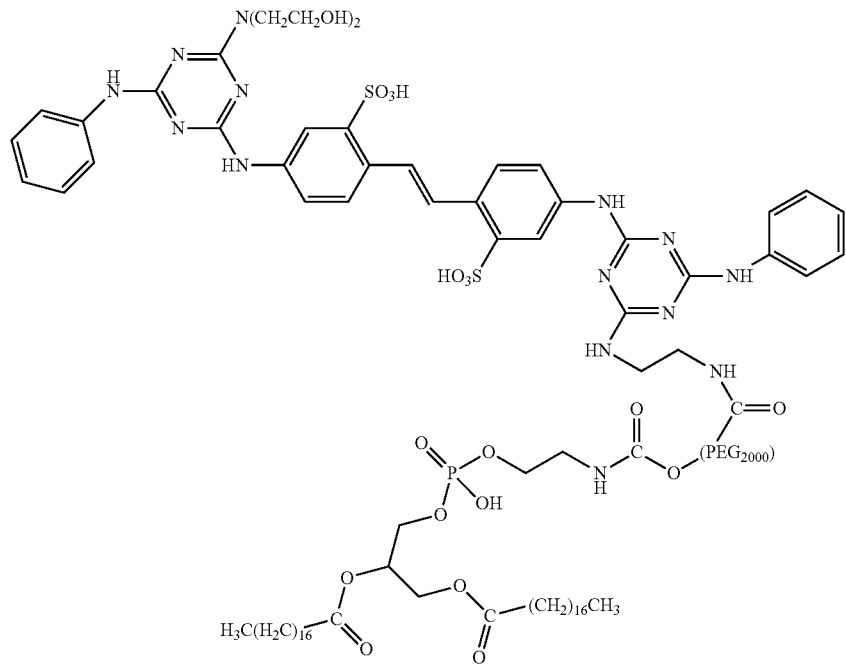

An alternative approach was to assemble TA-124-TA-127 by introducing the PEG unit onto the stilbene moiety prior to coupling with the phospholipid. One advantage in this approach was the ability to introduce a variety of fatty acid side chains into the TA-modified phospholipids, including changes in length and inclusion of unsaturation. DOPE was example. Those schooled in the art will readily recognize that any of the stilbene derivatives with a linker group could be coupled to DOPE or other phospholipids employing this approach.

Synthesis of stilbene-targeted phospholipid was initiated with

TA-124

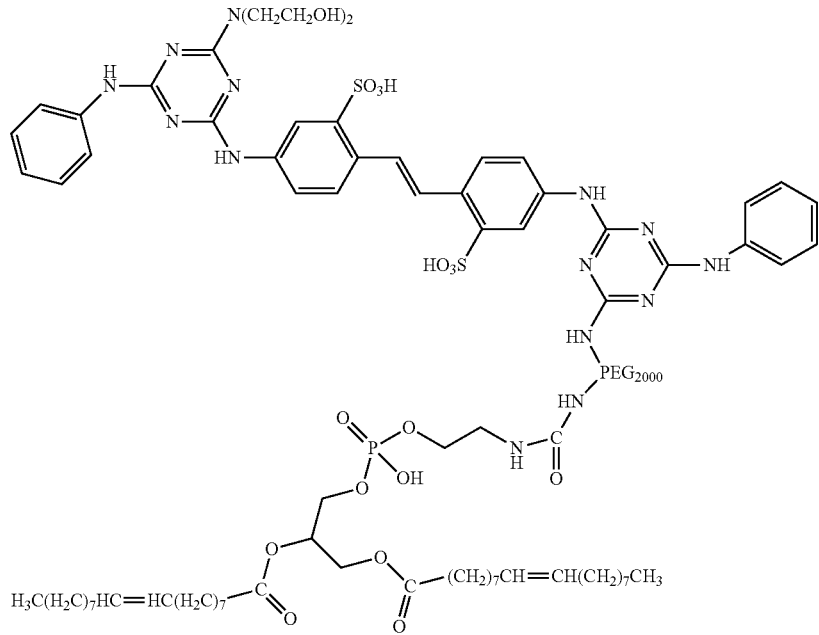

DSPE, 100 mg, and 6 eq TEA. The sample was dispersed in 2 mL CHCl₃ and 1.2 eq DSC added. The reaction mixture was stirred at room temperature for 2-3 h at which time the lipid and DSC went into solution. TLC was used to monitor completion of the reaction. An equal volume of DMF containing 3 eq of TA-111 and 3 eq of TEA was added. The reaction was carried out with stirring at 55° C. for 20 h. The product, TA-128, was purified by preparative TLC three times. The overall yield was 45% (based on DSPE).

and sonicated for 30 min. The almost completely clear sample was filtered (PES, 0.22 m) to remove insoluble Am B.

Cell killing was more active with targeted liposomes compared to non-targeted liposome controls. However, the efficiency of cell killing was lower with liposomes than micelles, likely due to their larger size that may have resulted in fewer particles able to penetrate the cell wall of the yeast.

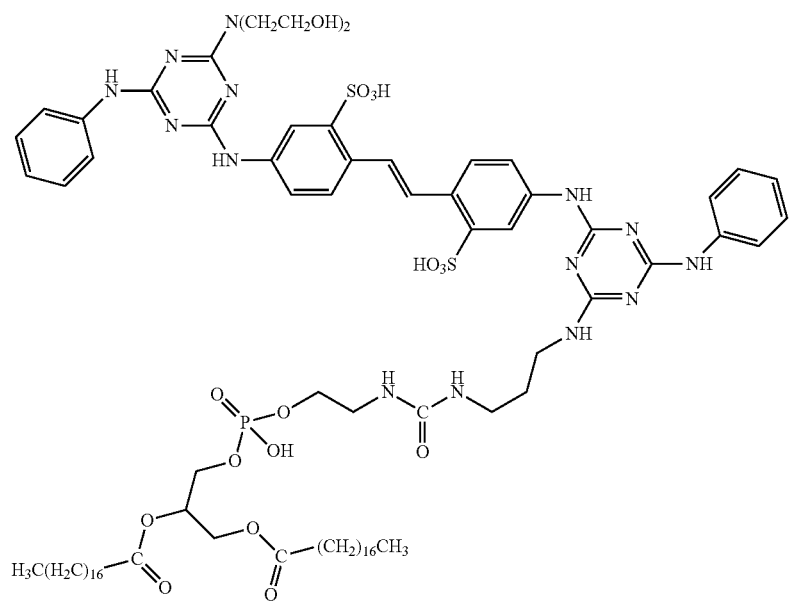

TA-128

Targeted Drug Delivery: Micelles

Targeted micelles were self-assembled from TA-122, TA-123, and TA-124 by procedures outlined in the literature (12) with equivalent results for each TA. As an example, TA-122 (1 μmol) was dissolved in 1 mL of CHCl₃ containing 4 μmol DSPE-PEG₂₀₀₀-OCH₃ and 5.78 μL (40 μg/μL) Am B in DMSO (5% Am B by weight based on total lipid). The bulk of the solvent was removed with N₂ and residual solvent removed by placing the sample under high vacuum for 1 h. After adding 1 mL PBS, the sample was vortexed for 20 min, then placed in a water bath at 55° C. for 30 min. The almost clear sample was finally put through a PES filter (0.22 μm) to remove insoluble Am B. The filtered sample was optically clear. A companion control was prepared minus the TA-122.

The killing efficiency of the targeted and non-targeted Am B micelles were compared in cultures of *Saccharomyces cerevisiae*. Growth inibition curves, as a function of drug concentration, revealed that targeted micelles required 5-fold less Am B to kill *S. cerevisiae* than non-targeted micelles, and at the high end of the curves, targeted micelles killed a larger proportion of fungal cells (92 versus 86%).

Targeted Drug Delivery: Liposomes

TA-128 was employed to assemble chitin-targeted liposomes. DSPC, TA-128, and Am B (in DMSO) were dissolved in CHCl and transferred to a round bottom flask. The solvent was removed on a rotary evaporator with the flask maintained at 55° C. PBS was added to the flask and the rotation of the flask in the bath continued (at ambient pressure) for 1 h. The sample was transferred to a test tube Targeted Drug Delivery: Nanodiscs TA-128 was used to assemble targeted nanodiscs by adapting procedures outlined in the literature (13). DMPC (2.8 mg), DMPG (1.2 mg), and 1 mg TA-128 were dissolved in CHCl₃/MeOH 3/1 and dried with N₂. The tube containing the lipids was placed on high vacuum for 1 h. PBS (0.5 mL) was added to the lipids and the sample vortexed. Am B (2.5 mg in 83 μL DMSO) was added and mixed. ApoA1 (3 mg in 3 mL PBS) was then added and the sample incubated overnight at room temperature. After mild sonication for 1-2 min, the sample was dialyzed (overnight) and filter sterilized.

The targeted nanodiscs were very active at killing *S. cerevisiae* in liquid cultures compared to non-targeted nanodiscs, with activity near that of micelles.

Targeted Drug Delivery: Dendrimers

G5 PAMAM-NH₂ dendrimers were obtained commercially and the surface groups activated with DSC. DSC (0.4 eq) was added to G5 dendrimers (1 μmol in 1 mL MeOH) and activation carried out at room temperature for 2 h. TA-111 (1.2 eq) was added in 0.5 mL DMF and the mixture stirred for 1.5 days at 35° C. The solvent was partially removed and the sample diluted with 3 mL PBS. The sample was extensively dialyzed against PBS. Sequestration of Am B by dendrimers was carried out as essentially described (14). Am B (3 mg) was added in DMSO, the sample vortexed, and shaken at room temperature overnight to equilibrate the drug with the dendrimers. After dialysis overnight against PBS, the amount of TA-111 and Am B incorporated into the dendrimers was determined spectrophotometrically.

Chitin-targeted dendrimers were very efficient at killing *S. cerevisiae* in liquid cultures compared to non-targeted dendrimers and activity was similar to that obtained with targeted-micelles.

REFERENCES

1. Castellani, R. J., Siedlak, S. L., Fortino, A. E., Perry, G., Ghetti, B. and Smith, M. A. (2005) Chitin-like polysaccharides in Alzheimer's disease brains. *Curr Alzheimer Res* 2, 419-423.
2. Castellani, R. J., Rolston, R. K. and Smith, M. A. (2010) Alzheimer Disease. *Dis Mon* 56, 484-546.
3. Sotgiu, S., Musumeci, S., Marconi, S., Gini, B. and Bonetti, B. (2008) Different content of chitin-like polysaccharides in multiple sclerosis and Alzheimer's disease brains. *J Neuroimmunol* 197, 70-73.
4. Wattenberg, L. W., Patterson, S. and Antonides, J. D. (2010) Chitin or Chitin-like Glycans as Targets for Late-term Cancer Chemoprevention. *Cancer Prev Res (Phila)* 3, 1519-1522.
5. Cunto-Amesty, G., Dam, T. K., Luo, P., Monzavi-Karbassi, B., Brewer, C. F., Van Cott, T. C. and Kieber-Emmons, T. (2001) Directing the immune response to carbohydrate antigens. *J Biol Chem* 276, 30490-30498.
6. Reverberi, R. and Reverberi, L. (2007) Factors affecting the antigen-antibody reaction. *Blood Transfus* 5, 227-240.
7. Weiner, L. M. and Adams, G. P. (2000) New approaches to antibody therapy. *Oncogene* 19, 6144-6151.
8. Cogan, U., Kopelman, M., Mokady, S. and Shinitzky, M. (1976) Binding affinities of retinol and related compounds to retinol binding proteins. *Eur J Biochem* 65, 71-78.
9. Samuel, M., Pixley, R. A., Villanueva, M. A., Colman, R. W. and Villanueva, G. B. (1992) Human factor XII (Hageman factor) autoactivation by dextran sulfate. Circular dichroism, fluorescence, and ultraviolet difference spectroscopic studies. *J Biol Chem* 267, 19691-19697.
10. Mulder, A., Huskens, J. and Reinhoudt, D. N. (2004) Multivalency in supramolecular chemistry and nanofabrication. *Organic & Biomolecular Chemistry Org. Biomol. Chem.* 2, 3409-3424.
11. de Hoog, P., Gamez, P., Driessen, W. L. and Reedijk, J. (2002) New polydentate and polynucleating N-donor ligands from amines and 2,4,6-trichloro-1,3,5-triazine. *Tetrahedron Lett* 43, 6783-6786.
12. Wang, Y., Wang, R., Lu, X., Lu, W., Zhang, C. and Liang, W. (2010) Pegylated phospholipids-based self-assembly with water-soluble drugs. *Pharm Res* 27, 361-370.
13. Oda, M. N., Hargreaves, P. L., Beckstead, J. A., Redmond, K. A., van Antwerpen, R. and Ryan, R. O. (2006) Reconstituted high density lipoprotein enriched with the polyene antibiotic amphotericin B. *J Lipid Res* 47, 260-267.
14. Gupta, U., Agashe, H. B. and Jain, N. K. (2007) Polypropylene imine dendrimer mediated solubility enhancement: effect of pH and functional groups of hydrophobes. *J Pharm Pharm Sci* 10, 358-367.

ABBREVIATIONS

ApoA1; Apolipoprotein A1
DEOA; diethanolamine
DOPE; dioleylphosphatidylethanolamine
DSC; disuccinimidylcarbonate
DSPC; distearoylphosphatidylcholine
DSPE; distearoylphosphatidylethanolamine
NMM; N-methylmorpholine
OBPA; stilbene optical brightener propylamine
PBS; physiological phosphate buffered saline, pH 7.5
PES; polyethersulfone
TEA; triethylamine

The invention claimed is:
1. A chitin targeting agent comprising the following structure:

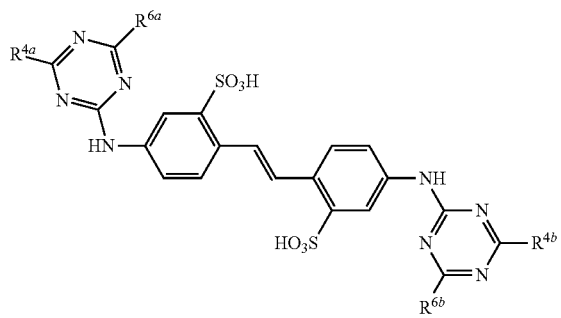

wherein $R^{4a}$, $R^{4b}$, and $R^{6a}$ are independently selected from Cl, amino, or hydroxy, the last two of which are optionally substituted by alkyl, alkylamino, alkylhydroxy, alicyclic, heterocyclic, aryl, and alkyl- or arylsulfonic acid, where each of the optional substituents may further be optionally substituted by one or more groups selected from the group consisting of hydroxy and amino,
wherein $R^{6b}$ is linked to phospholipid-$PEG_n$, where the number of PEG units, n, is about 10-250, phospholipid, or dendrimer ($G_3$-$G_{10}$),
wherein the linker is composed of PEG, alkyl, heteroalkyl, heterocyclic, or aryl, and pharmaceutically acceptable salts thereof.
2. A targeted drug delivery vehicle comprising the chitin targeting agent of claim 1, and further comprising a block copolymer micelle and one or more antifungal drugs.
3. A targeted drug delivery vehicle comprising the chitin targeting agent of claim 1, and further comprising a liposome and one or more antifungal drugs.
4. A targeted drug delivery vehicle comprising the chitin targeting agent of claim 1, and further comprising a nanodisc and one or more antifungal drugs.
5. A targeted drug delivery vehicle comprising the chitin targeting agent of claim 1, and further comprising a dendrimer and one or more antifungal drugs.
6. A targeted drug delivery vehicle comprising the chitin targeting agent as in one of claims 2-5 wherein the antifungal drug consists of Amphotericin B.
7. A targeted drug delivery vehicle comprising the chitin targeting agent as in one of claims 2-5 wherein the antifungal drug is selected from the group consisting of an echinocandin, azole, allosamidin, anidulafungin, bifonazole, butenafine, butoconazole, candicidin, caspofungin, cerulenin, chloroxine, ciclopirox, clioquinol, clotrimazole, econazole, fluconazole, flucytosine, griseofulvin, itraconazole, ketoconazole, micafungin, miconazole, naftifine, natamycin, nystatin, oxiconazole, posaconazole, sertaconazole, terbinafine, terconazole, tioconazole, and voriconazole.
8. A targeted drug delivery vehicle comprising the chitin targeting agent as in one of claims 2-5 and further comprising a block copolymer micelle and one or more antifungal drugs, and one or more phospholipids.

9. A targeted drug delivery vehicle comprising the chitin targeting agent as in one of claims 2-5 and further comprising a liposome and one or more antifungal drugs, and one or more phospholipids.

10. A targeted drug delivery vehicle comprising the chitin targeting agent as in one of claims 2-5 and further comprising a nanodisc and one or more antifungal drugs, and one or more phospholipids.

11. A method of preparing a targeted drug delivery vehicle, comprising assembling into a micelle, liposome or nanodisc a phospholipid, a targeting agent of claim 1 and an antifungal drug wherein the phospholipid comprises phosphatidylethanolamine.

12. A method of preparing a targeted drug delivery vehicle, comprising assembling into a micelle, liposome or nanodisc a phospholipid, a targeting agent of claim 1 and an antifungal drug wherein the phospholipid comprises phosphatidylserine, phosphatidylinositol, phosphatidylinositol phosphate, phosphatidylglycerol, or phosphatidylglycerol phosphate, optionally covalently linked to polyethylene glycol.

\* \* \* \* \*